United States Patent [19]

Alfano et al.

[11] Patent Number: 5,131,398

[45] Date of Patent: Jul. 21, 1992

[54] METHOD AND APPARATUS FOR DISTINGUISHING CANCEROUS TISSUE FROM BENIGN TUMOR TISSUE, BENIGN TISSUE OR NORMAL TISSUE USING NATIVE FLUORESCENCE

[75] Inventors: Robert R. Alfano, Bronx; Bidyut Das, Flushing; Guichen Tang, New York, all of N.Y.

[73] Assignee: Mediscience Technology Corp., Whitehouse State, N.J.

[21] Appl. No.: 468,633

[22] Filed: Jan. 22, 1990

[51] Int. Cl.⁵ ............................................. A61B 6/00
[52] U.S. Cl. .................................. 128/665; 128/395; 128/398
[58] Field of Search ............... 128/633, 634, 665, 395, 128/398; 356/435; 606/3, 15, 16

[56] References Cited

U.S. PATENT DOCUMENTS

| | | | |
|---|---|---|---|
| 4,479,499 | 10/1984 | Alfano | 128/665 |
| 4,930,516 | 6/1990 | Alfano et al. | 128/665 |
| 4,957,114 | 9/1990 | Zeng et al. | 128/665 |
| 4,981,138 | 1/1991 | Deckelbaum et al. | 128/665 |

FOREIGN PATENT DOCUMENTS 2-22331 7/1983 Japan.

OTHER PUBLICATIONS

G. C. Tang et al., Applied Optics, vol. 28, No. 12, pp. 2337-2342 (Jun. 1989).

*Primary Examiner*—Ruth S. Smith
*Attorney, Agent, or Firm*—Kriegsman & Kriegsman

[57] ABSTRACT

A method and apparatus for distingishing cancerous tumors and tissue from benign tumors and tissue or normal tissue using native fluorescence. The tissue to be examined is excited with a beam of monochromatic light at 300 nanometers (nm). The intensity of the native fluorescence emitted from tissue is measured at 340 and 440 nm. The ratio of the two intensities is then calculated and used as a basis for determining if the tissue is cancerous as opposed to benign or normal. The invention is based on the discovery that when tissue is excited with monochromatic light at 300 nm, the native fluorescence spectrum over the region from about 320 nm to 600 nm is the tissue that is cancerous and substantially different from the native fluorescence spectrum that would result if the tissue is either benign or normal. The technique is useful in invivo and in vitro testing of human as well as animal tissue.

2 Claims, 12 Drawing Sheets

METHOD AND APPARATUS FOR DISTINGUISHING CANCEROUS TISSUE FROM BENIGN TUMOR TISSUE, BENIGN TISSUE OR NORMAL TISSUE USING NATIVE FLUORESCENCE

This invention was made with Government support under Contract N00014-87-K-0431 awarded by the Department of the Navy. The Government has certain rights in this invention.

BACKGROUND OF THE INVENTION

The present invention relates to a method and apparatus for distinguishing cancerous tissue from benign tumor tissue, benign tissue or normal tissue and more particularly to a method and apparatus for distinguishing cancerous tissue from benign tumor tissue, benign tissue or normal tissue using native fluorescence. As used herein, the term "cancerous tissue" includes cancerous tumor tissue.

Because a sufficiently effective method has not yet been developed to prevent cancer, cancer research has focused primarily on the most effective ways to diagnose and treat cancer. As different as the various forms of treatment have been—ranging from excision to radiation to chemotherapy—all treatments have relied on one crucial step, detection of the tissue that is cancerous. The importance of detection cannot be stressed enough. Early detection not only indicates the presence of a cancer but also may give an indication as to where the cancer originated and as to what type of treatment will be the most safe and effective method. Early detection can provide such benefits because it reveals the state of maturation of the cancer cell. Cancer cells are clonal cells of a single "founder" cell that is the result of some mutation of the normal cell for the particular tissue. As a result of the mutation, the founder cell replicates and divides, eventually forming a mass of cells called a tumor. Cancerous tumors are harmful because they proliferate at a metabolic rate that exceeds that of the normal neighboring cells. As a result, the cancerous tumor grows at the expense of the normal neighboring tissue, ultimately destroying the normal tissue. One of the reasons why it is so difficult to completely cure cancer is that cancer cells have the ability to disseminate throughout the body via lymphatic or circulatory systems and to create new tumors where they arrive. However, this ability to disseminate comes only to those cells that have lost the characteristic membrane glycoproteins of the mutated tissue. For this reason, it takes a while before cancer can spread. An advantage to early detection is that the cells can be examined for characteristic properties such as cell size and shape to determine the source of the cancer cells.

It should be noted that in addition to tumors which are cancerous, there are tumors which are non-cancerous. Non-cancerous tumors are commonly referred to as benign tumors.

Clearly, the importance of an accurate technique that can be utilized either in vivo or in vitro for detecting cancerous tumors cannot be minimized. The advantage of an in vivo technique is that sensitive tissue may be tested, relatively undisturbed, for example, with the use of an inserted optical fiber probe. An article entitled, "Gastrointestinal Endoscopy" appearing in *Clinical Symposia* Vol. 32, Number 3 delineates the possible use for such a method of detecting cancer. As another example, an endoscope can be used to test tissue in vivo.

In copending U.S. patent application Ser. No. 186,747 filed on Apr. 25, 1988 in the name of Robert R. Alfano et al there is disclosed a method and apparatus for distinguishing between cancerous and normal tissue using native visible fluorescence. The technique involves exciting the tissue with a beam of monochromatic light having a wavelength of about 488 nanometers (nm) and then measuring the intensity of the fluorescence produced over a spectral region from about 500 to 700 nanometers.

Although the above technique is useful in distinguishing cancerous from normal tissue it does not distinguish cancerous tissue from benign tissue and benign tumor tissue. In some cases, samples of benign tissue and benign tumor tissue that have been tested using the technique produced spectral profiles similar to cancerous tissue or cancerous tumors and in other cases samples of benign tissue and benign tumor tissue produced spectral profiles similar to normal tissue using the above noted 488 excitation.

As can be appreciated, the key behind a spectroscopic technique for detecting cancer involves being able to distinguish between cancerous and benign tissue and benign tumor tissue as well as between cancerous and normal tissue.

In U.S. Pat. No. 4,718,417 to Kittrell et al there is disclosed a method of distinguishing artery wall from atherometous plaque or other material using visible fluorescence induced by 480 nm exciting light.

In U.S. Pat. No. 4,785,806 to L. I. Deckelbaum there is disclosed a method of ablating atherosclerotic tissue in which a fluorescence pattern of the tissue obtained by UV excitation is first examined to see if it is normal or abnormal.

Other known references of interest are U.S. Pat. No. 4,290,433 to Robert R. Alfano, U.S. Pat. No. 4,479,499 to Robert R. Alfano and U.S. Pat. No. 4,566,057 to T. Hiruma et al.

SUMMARY OF THE INVENTION

It is an object of this invention to provide a new and improved technique for distinguishing cancerous tissue from noncancerous tissue.

It is another object of the invention to provide a technique for distinguishing cancerous tissue from benign tissue and benign tumor tissue.

It is yet another object of this invention to provide a technique for distinguishing cancerous tissue from benign tissue, benign tumor tissue or normal tissue.

It is still another object of this invention to provide a technique for distinguishing cancerous tissue from benign tissue, benign tumor tissue or normal tissue using native fluorescence.

It is further object of this invention to provide a technique for distinguishing cancerous tissue from benign tissue, benign tumor tissue or normal tissue which does not require the use of X-ray sensitive plates or film.

It is still a further object of this invention to provide a in-vivo spectroscopy diagnosis technique to determine the presence of cancer inside a body (i.e. breast, cervex, uterus, lungs, urinary tract, vagina, intestinal tract, stomach, brain, colon, eye and throat etc.).

It is still a further object of this invention to provide a in-vitro spectroscopy diagnostic technique for testing biopsy tissue samples to determine if they are cancerous as opposed to benign or normal.

It is yet still another object of this invention to provide a technique as described above in which the effects of blood which alters the fluorescence spectrum by absorption from the tissue are reduced or eliminated.

The present invention is based on the discovery that when excited with a beam of monochromatic light at 300 nm. the native fluorescence spectrum for cancerous tissue, benign tissue (tumorous or non-tumorous) and normal tissue are significantly different and more specifically are significantly different when observed over the fluorescent spectral region from about 320 to about 600 nm. As a result of these differences, one can effectively distinguish cancerous tissue and tumors from benign tissue and tumors or normal tissue. Any one of a number of techniques may be employed for making these distinctions. These include (1) taking the ratio of two (or more) emission wavelengths and seeing if the value is above or below a predetermined number, or (2) taking the difference of two (or more) emission wavelengths and seeing if the value is above or below a predetermined number, or (3) comparing the profile obtained with profiles of samples of tissue whose condition is known.

According to another feature of the invention the effects of absorption from blood which alters the fluorescence spectrum from the tissue can be reduced or even eliminated by taking readings to determine the tissue condition at wavelengths where the amount of absorption from blood is the same.

A method for distinguishing cancerous tissue and from benign tumor tissue, benign tissue or normal tissue according to the teachings of this invention and based on the above noted discovery involves, according to one embodiment of the invention, illuminating a region to be examined with a beam of monochromatic light at about 300 nm, measuring the intensity of the native fluorescence at about 340 and 440 nm. and then using that ratio of the intensities at those two wavelengths to determine if the material under test tissue is cancerous as opposed to benign or normal.

An apparatus for determining if tissue is cancerous as opposed to normal or benign according to the teachings of this invention and based on the above noted discovery, according to one embodiment of the invention, includes a light source for emitting a beam of monochomatic light at about 300 nm, a pair of filtered photodetectors, one for receiving light only at about 340 nm and the other for receiving light only at 440 nm, means for directing the light from the source onto the tissue and the light emitted therefrom to each one of the photodetectors, an analog to digital converter coupled to the outputs of the filtered photodetectors for digitizing the output signals from the photodetectors and a computer coupled to the output of the analog to digital converter for processing the two digital output signals from the analog to digital converter.

The excitation light need not be exactly monochromatic, but rather can have a bandwidth on the order of about 20 nm. The detected light can also have a bandwidth on the order of about 20 nm. The excitation light is not limited to 300 nm but, as will hereinafter be shown, can be from about 260 nm to 315 nm.

If performing in vitro testing, the apparatus may further include a bar coder so that samples may be bar coded and along with the results obtained stored in the computer for later use.

The invention may be used in both invivo and invitro testing of human as well as animal tissue.

The foregoing and other objects and advantages will appear from the description to follow. In the description, reference is made to the accompanying drawing which forms a part thereof, and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

DETAILED DESCRIPTION

The present invention is directed to a method and apparatus for distinguishing cancerous tissue from benign tissue, benign tumor tissue or normal tissue using native fluorescence.

The present invention is based on the above noted discovery that the native fluorescent spectrum from about 320 nm to about 600 nm at 300 nm excitation for cancerous human tissue is significantly different than that of benign human tissue, benign human tumor tissue or normal human tissue and that through these differences one can distinguish cancerous human tissue from benign tumors or tissue or normal human tissue.

The differences in the spectra can be used to distinguish cancerous from benign or normal tissue in any one of a number of ways. For example, one can take the ratio of the intensity at two emission wavelengths and see if it falls about or below a predetermined value. As another example, one can take the difference in the intensities at two emission wavelengths and see if it falls above or below a predetermined value. As still another way, a person can compare the spectral profile with the existing profile for a known tissue. Instead of emission profiles, excitation profiles may be employed to distinguish cancerous tissue from benign or normal tissue. When taking differences or comparing profiles, the spectra are first normalized. When taking ratios or comparing profiles, the spectra may be normalized; however, this is not essential.

In all of the data hereinafter set forth, the spectra were obtained using a Perkin Elmer Lamp Fluorescene And Excitation LS50 instrument.

Figure 1:
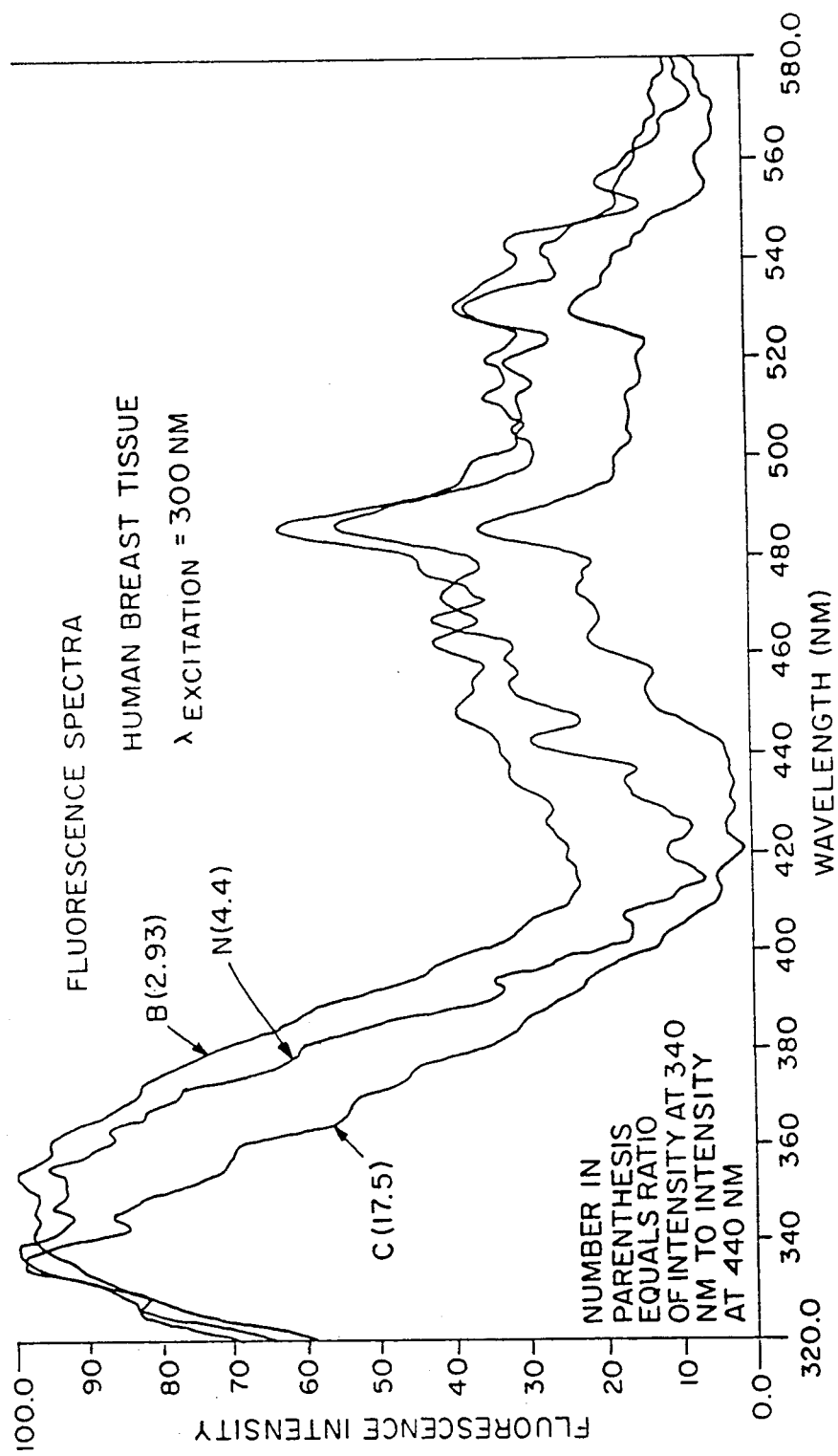
FIG. 1 are fluorescence spectra at 300 nm excitation of a sample of normal human breast tissue (N), a sample of benign human breast tumor tissue (B) and a sample of cancerous human breast tissue (C)

Referring now to FIG. 1 there are shown the fluorescence spectra from 320 to 580 nm at 300 nm excitation for a sample of cancerous human breast tissue (Curve C), a sample of benign human breast tumor tissue (Curve B) and a sample of normal human breast tissue (Curve N). As can be seen the spectra are substantially different. Because of these differences, one can effectively distinguish cancerous tissue from benign or normal tissue.

As noted above, one can either take the ratio of two emission wavelengths and see if it is greater or less than a predetermined value, take the difference of two emission wavelength and see if it is greater or less than a predetermined value or compare the spectral profile with a known profile.

In samples that have been so tested, it has been found that the fluorescence readings can be altered as a result of absorption of some of the fluorescence by blood in the vicinity of the region of the tissue being examined.

According to another feature of this invention, alterations in the readings caused by absorption of the fluorescence emitted from tissues by blood can be essentially eliminated by taking readings at wavelengths where the amount of absorption by blood is the same. By selecting wavelengths where absorption is the same, different amounts of blood which may present in the tissue or organ or surroundings can also be accounted for. This approach can reduce any variations in sample preparation or amount of bleeding in the area of the tumor or tissues. The intrinsic fluorescence fingerprint of cancer and benign tissue can be measured at these well selected absorption compensating wavelengths. Thus, in FIG. 1, the ratio of the intensity of 340 nm to the intensity at 440 nm for the cancerous sample is 17.5, for the benign sample is 2.93 and for the normal sample is 4.4.

Figure 2:
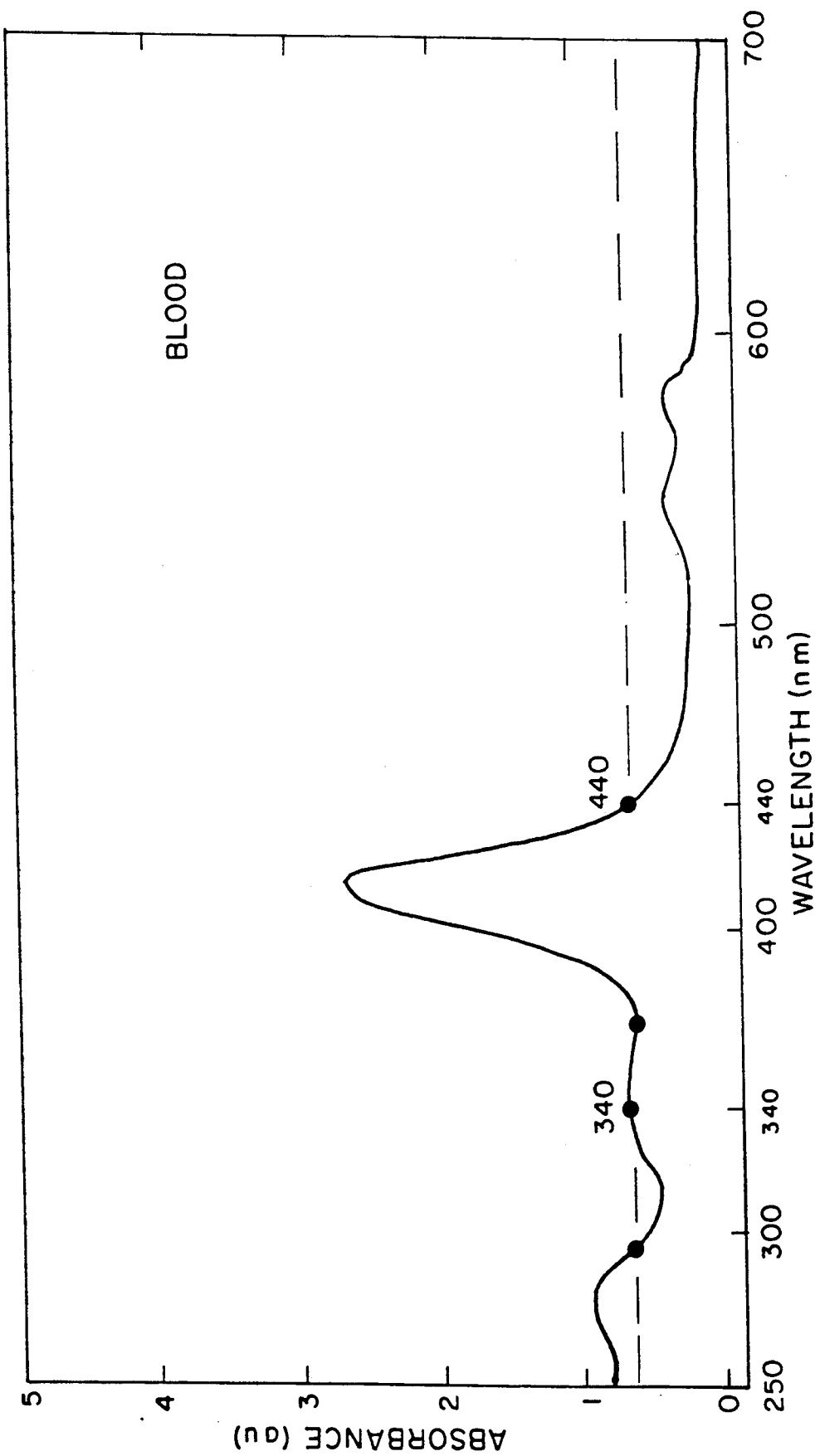
FIG. 2 a prior art chart of absorbance vs. wavelength of blood showing wavelengths where the absorption is the same.

FIG. 2 shows a prior art curve of the relative absorbance spectrum of blood from 250 nm to 700 nm. As can be seen, the same amount of absorbance occurs at for example about 340 nm, 360 nm and 440 nm.

By measuring the fluorescence intensity at these selected wavelengths, one can ignore the effect of the amount of absorption resulting from blood on the fluorescence intensity at these wavelengths.

Thus, by measuring the values of fluorescence intensity of at, for example, 340 nm and 440 nm one can distinguish between cancer and benign tissues by taking ratios or differences, etc. taking automatically into account the blood in these tissues.

Figure 3:
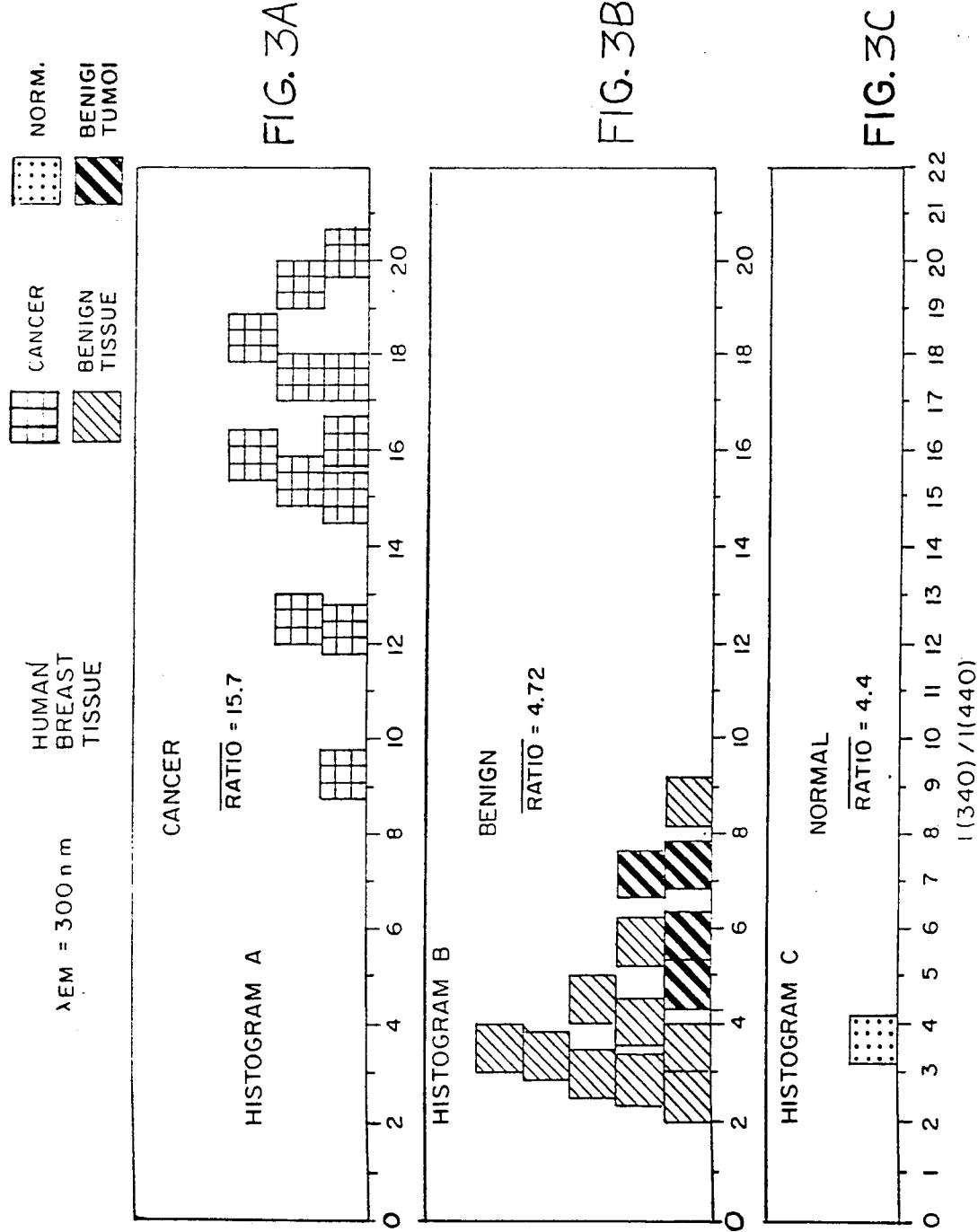
FIGS. 3A through 3C are ratio histograms of samples of normal human breast tissue, benign human breast tissue and benign human breast tumor tissue and cancerous human breast tissue.

Referring now to FIG. 3A there is shown a histogram labelled HISTOGRAM A prepared from twelve samples of cancerous human breast tissue, in FIG. 3B a histogram labelled HISTOGRAM B prepared from fourteen samples of benign human breast tumor tissue and benign human breast tissue and in FIG. 3C a histogram labelled HISTOGRAM C prepared from one sample of normal human breast tissue. As can be seen, benign human breast tissue samples and benign human breast tumor tissue samples are shown together in HISTOGRAM B. For each tissue sample, a ratio corresponding to the fluorescence at 340 nm divided by the fluorescence at 440 nm was calculated. Each sample was excited with 300 nm light. As can also be seen, the ratio for the cancerous samples averaged out to 15.7 and for the benign samples was 4.72. The ratio of the normal tissue was 4.4. Thus, a criteria can be established using these samples that, for example, a ratio of above 8 would mean cancerous and a ratio of below 8 would mean either benign or normal.

Figure 4:
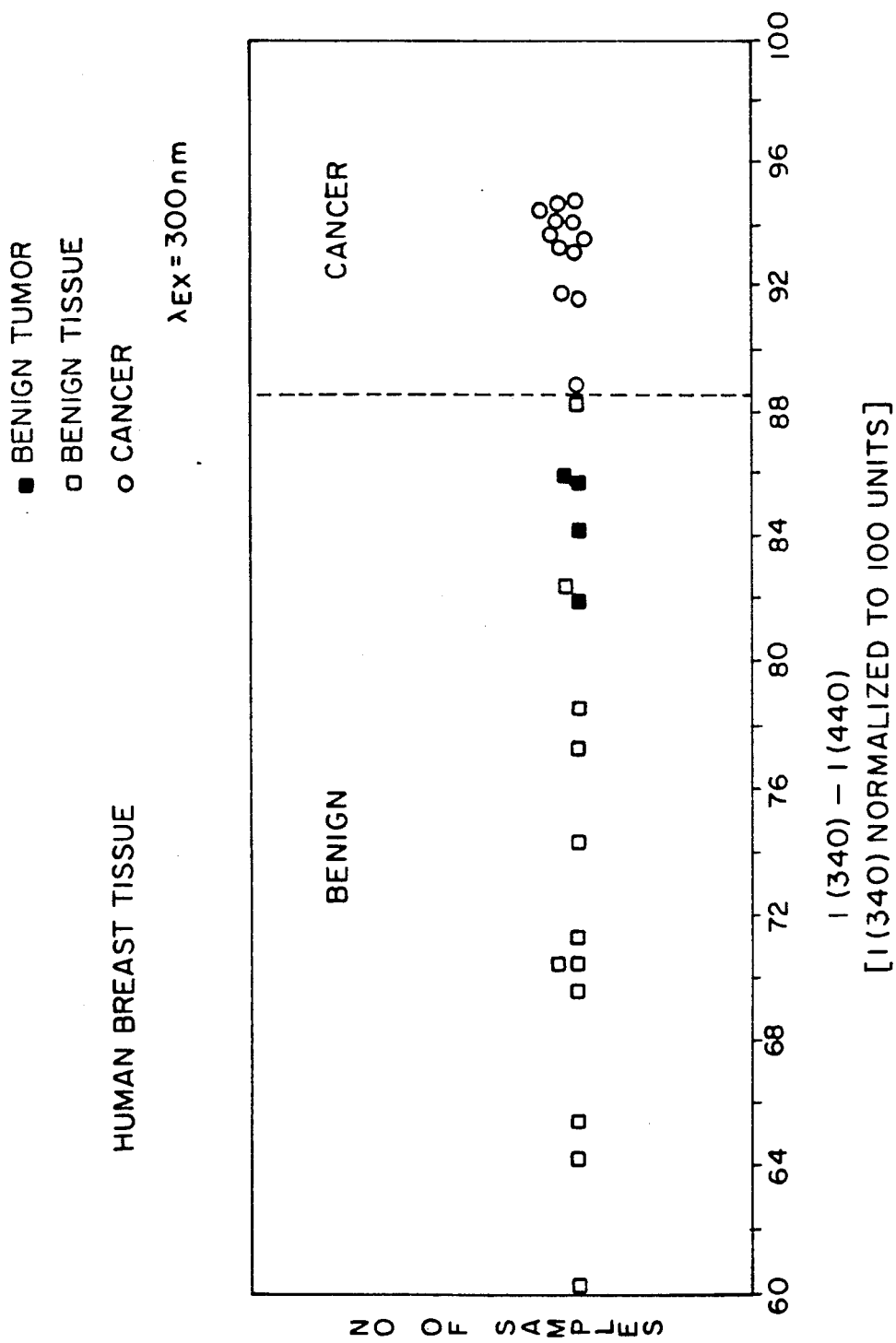
FIG. 4 are difference histograms of samples of normal human breast tissue, benign human breast tissue, benign human breast tumor tissue and cancerous human breast tissue.

Referring now to FIG. 4 there is shown a histogram prepared by taking the difference between the fluorescence intensity at 340 nm and the fluorescence intensity at 440 nm for twelve samples of cancerous human breast tissue and sixteen samples benign human breast tissue all excited with 300 nm light, with the readings normalized. As can be seen, the benign samples are all below 88 and the cancerous samples are all above 88.

Figure 5:
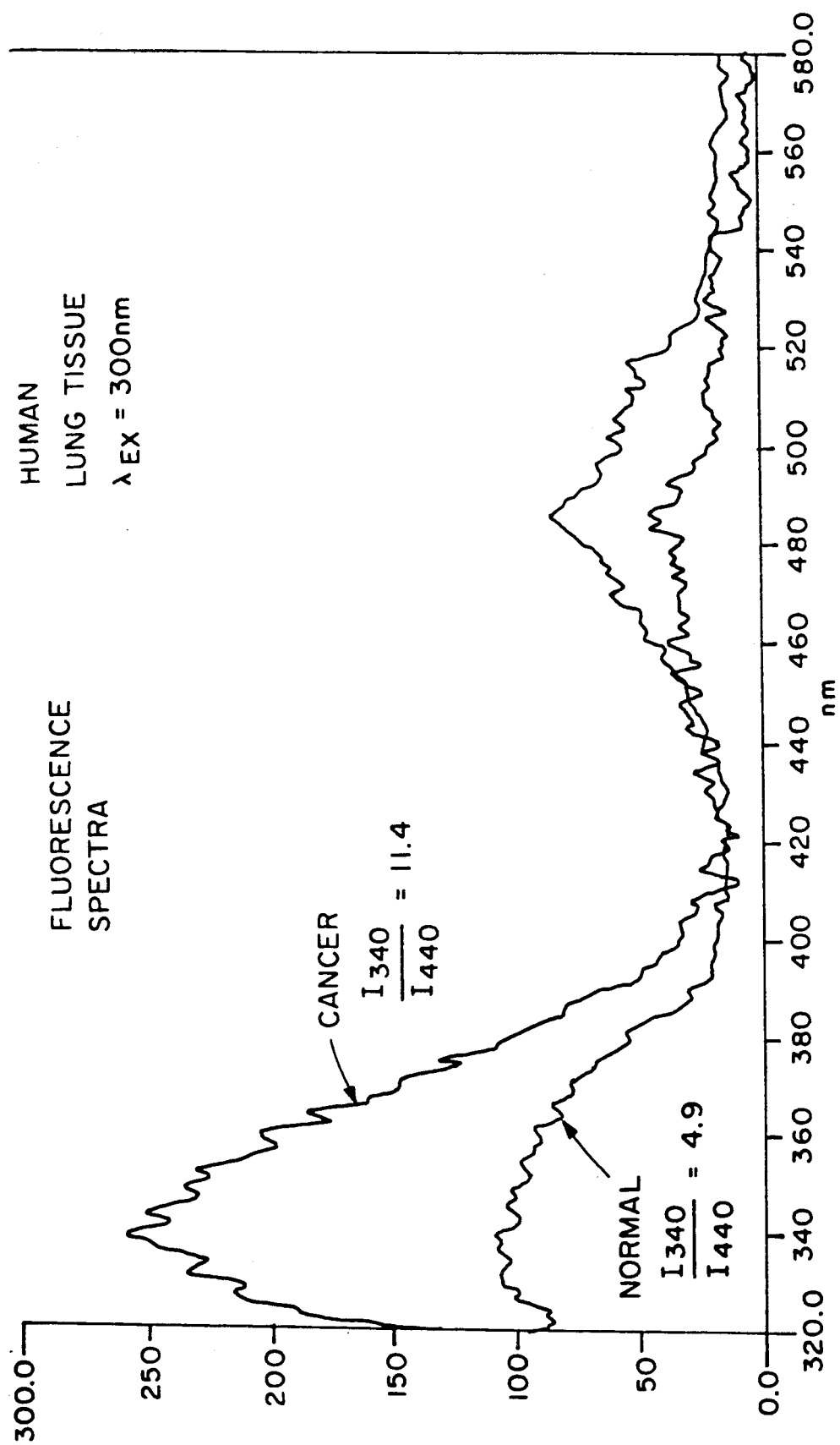
FIG. 5 are fluorescence spectra at 300 nm excitation for a sample of normal human lung tissue and a sample of cancerous human lung tissue.

Referring now to FIG. 5 there are shown the fluorescence spectra from 320 to 500 nm for a sample of human cancerous lung tissue and a sample of human normal lung tissue when excited with monochromatic light at 300 nm. As can be seen, the spectra are substantially different. The ratio for the cancerous tissue for 340 nm and 440 nm is greater than 8 while the ratio for the normal tissue is less than 8.

Figure 6:
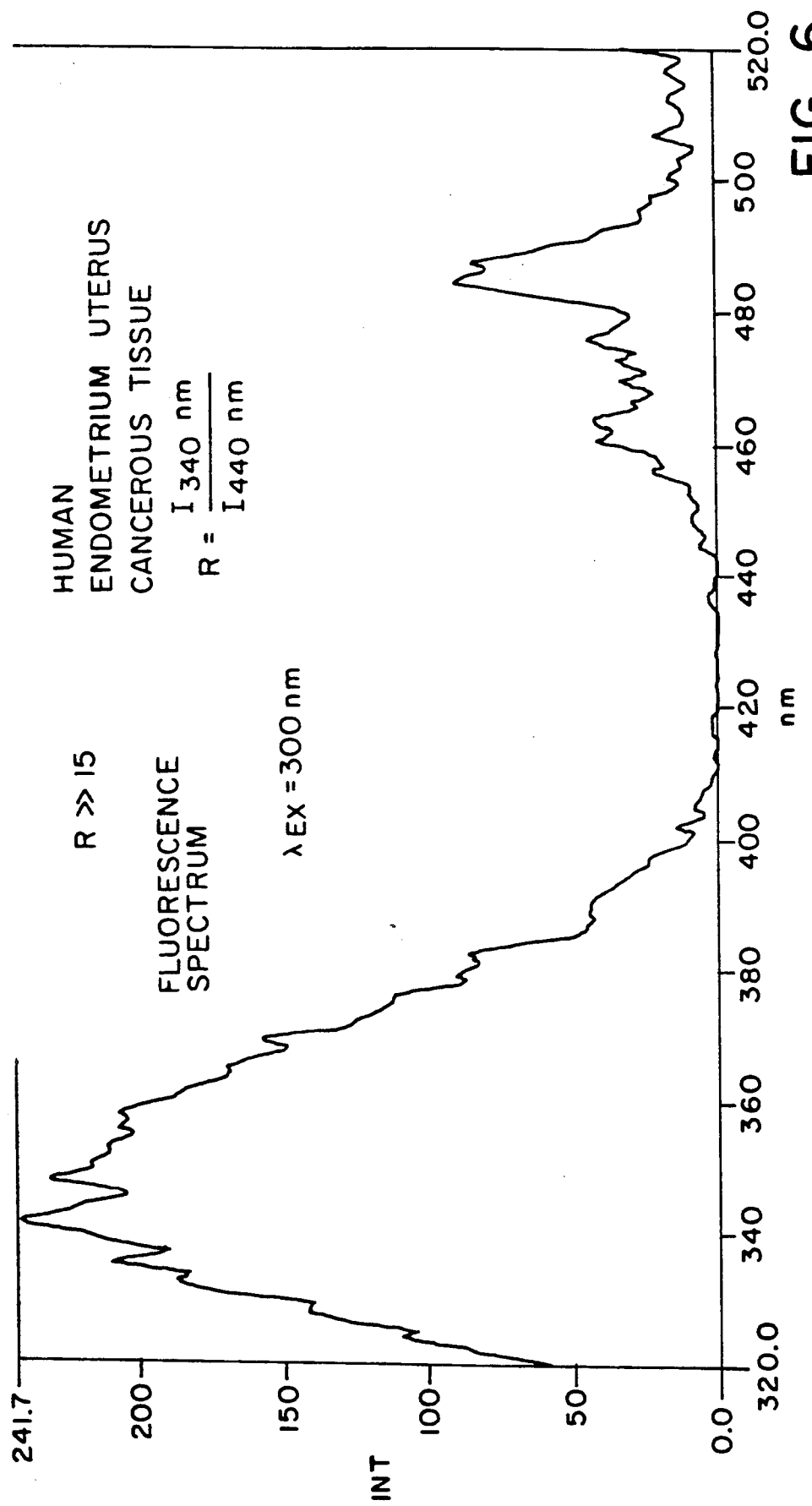
FIG. 6 is a fluorescence spectra at 300 nm excitation of a sample of cancerous human endometrum uterus tissue.
Figure 7:
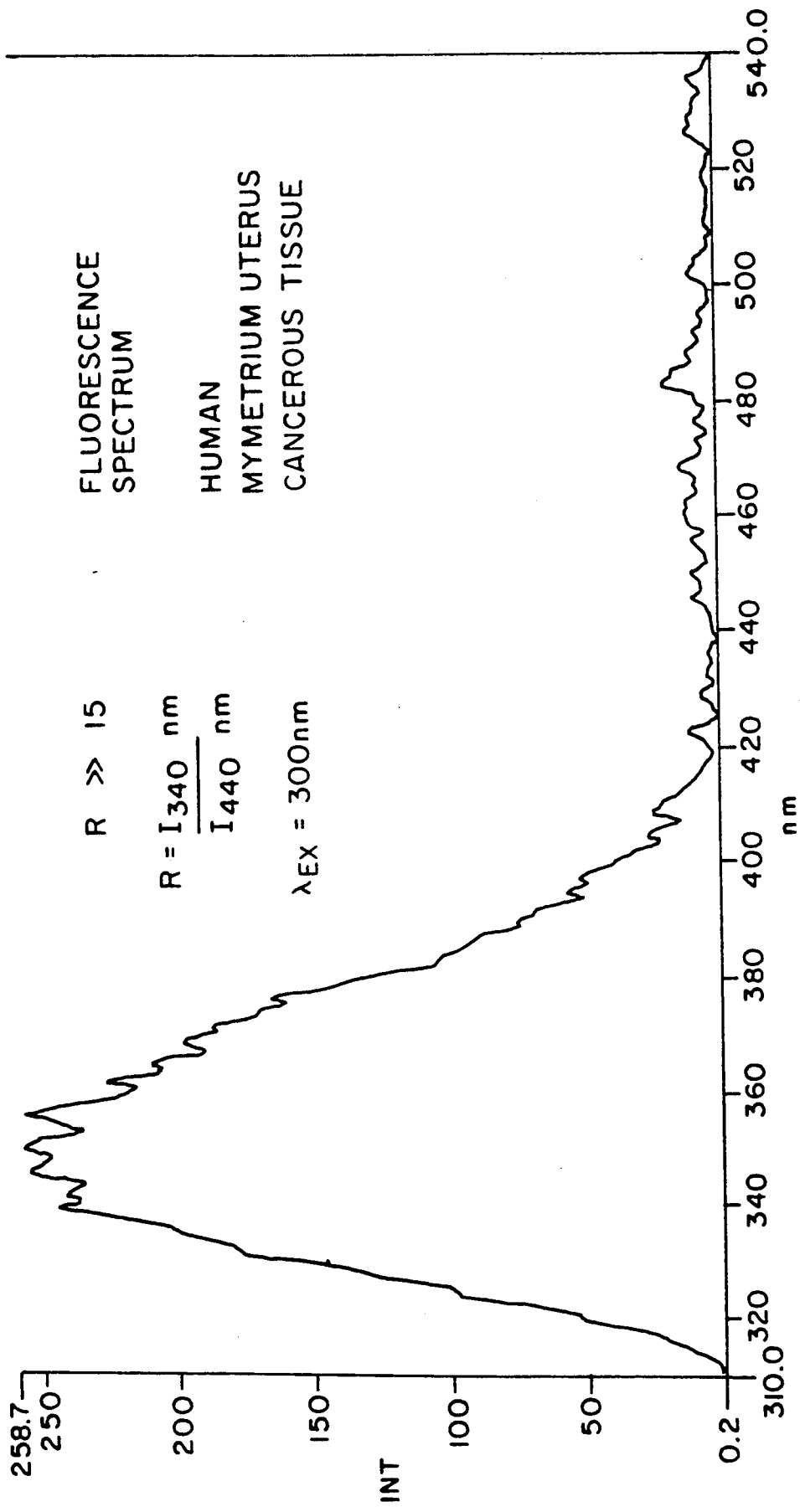
FIG. 7 is a fluorescence spectra at 300 nm excitation of a sample of cancerous human myetrium uterus tissue.

Referring now to FIGS. 6 and 7 there are shown fluorescence spectra obtained for a sample of human cancerous endometrium uterus tissue and a sample of human cancerous myetrium tissue, respectively. Both samples were excited with monochromatic light at 300 nm. The spectrum for the endometrium tissue is from 320 to 520 nm while the spectrum for the myetrium tissue is from 310 to 540. The ratio of the 340 nm reading to the 440 nm reading for both samples is much greater than 15.

Figure 8:
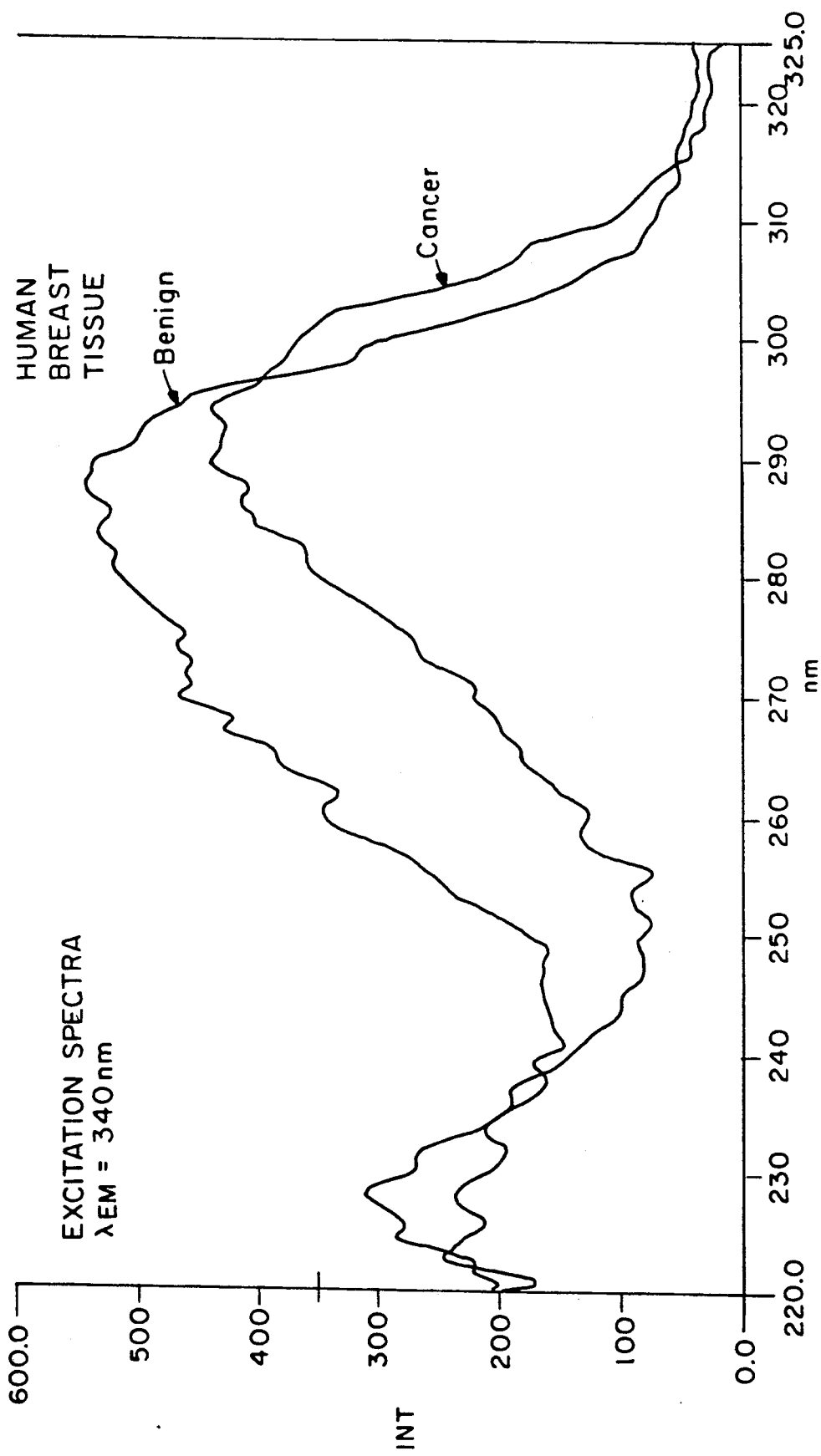
FIG. 8 are excitation spectra obtained for a sample of benign human breast tissue and for a sample of cancerous human breast tissue at an emission wavelength of 340 nm.
Figure 9:
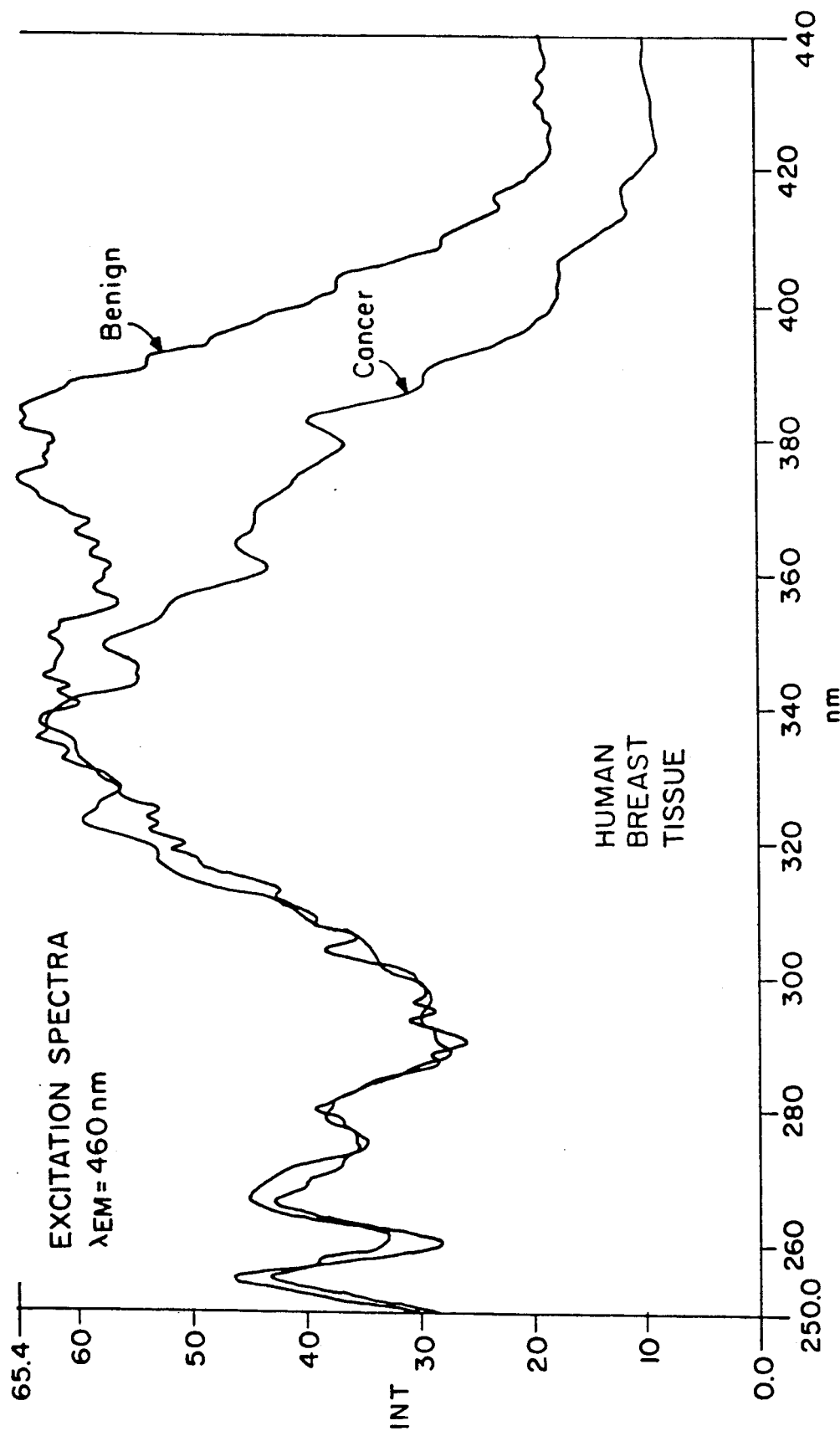
FIG. 9 are excitation spectra obtained for a sample of benign human breast tissue and for a sample of cancerous human breast tissue at an emission wavelength of 460 nm.

Referring now to FIG. 8, there is shown excitation spectra at an emission wavelength of 340 nm for a sample of cancerous breast tissue and a sample of benign breast tissue. As can be seen, the spectra are substantially different. The spectra were obtained by measuring the intensity of the fluorescence at 340 as the excitation wavelength was varied from 220 nm to 325 nm. Excitation spectra for two other samples at an emission wavelength of 460 nm are shown in FIG. 9.

Excitation spectra are useful in determining the range of excitation frequencies that can be used but can also be used for distinguishing cancerous from benign and normal in the same way as emission spectra are used, as described above.

Figure 10:
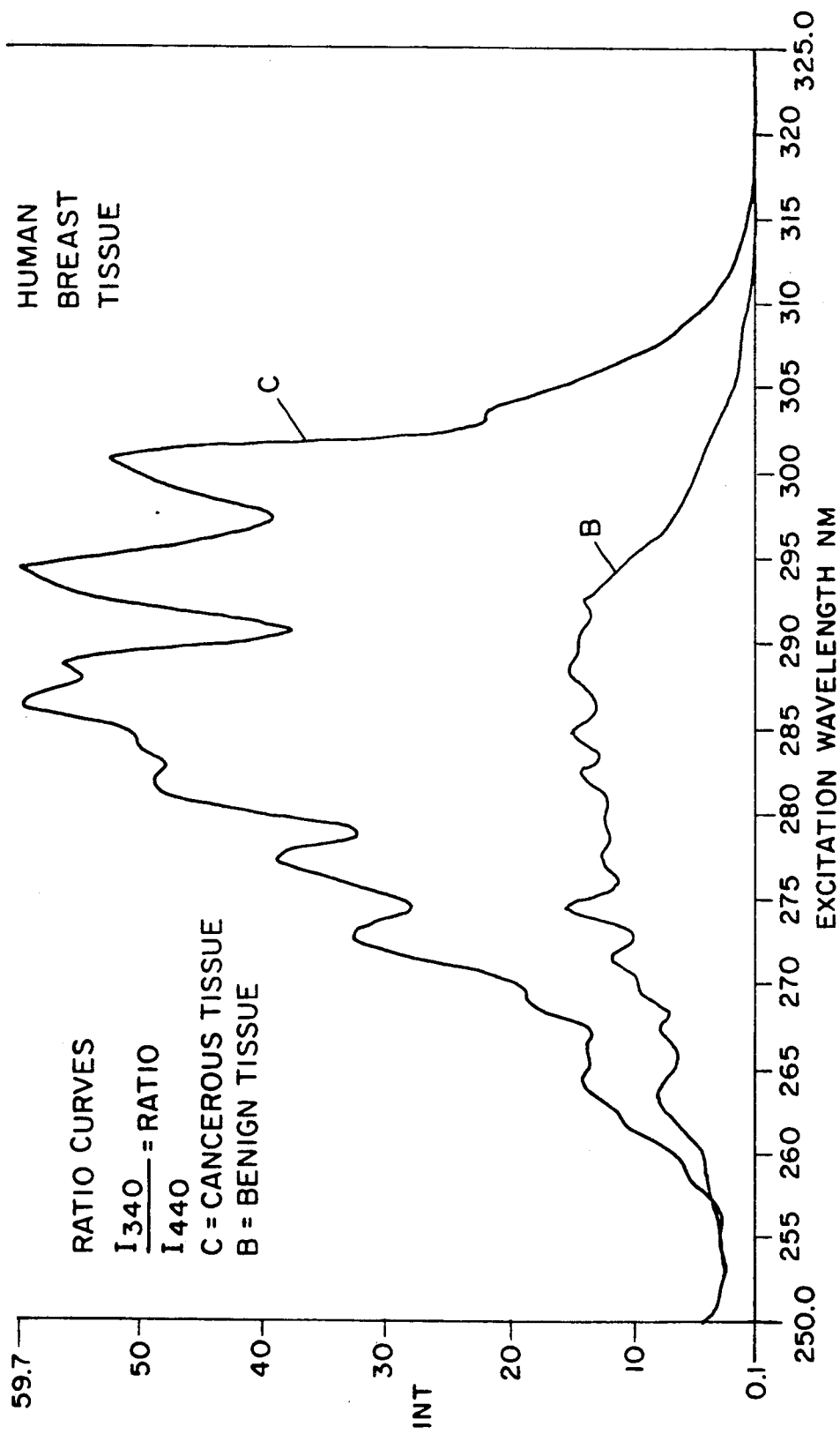
FIG. 10 are curves showing the ratio of the intensity of the fluorescence at 340 nm to the intensity of the fluorescence 440 nm for excitation wavelengths from 250 nm to 325 nm for a sample of cancerous breast tissue and for a sample of benign breast tissue.

Referring now to FIG. 10 there is shown a curve (C) of the ratio of the intensity of the fluorescence at 340 nm to the intensity of the fluorescence at 440 nm for excitation wavelengths from 250 nm to 325 nm for a sample of cancerous breast tissue and a curve (B) of the ratio for the intensity of the fluorescence at 340 nm to the intensity of fluorescence at 440 for excitation wavelengths from 250 nm to 325 nm for a sample of benign breast tissue. The curves show that excitation wavelengths between about 260-315 can be used to distinguish cancerous from benign tissue since the ratios are different and wavelengths above 315 nm show basically no difference. 300 nm excitation is preferably since it gives a significant ratio difference.

The optimum excitation wavelength maya vary slightly depending on the particular organ (i.e. breast lun, etc.) being tested.

Figure 11:
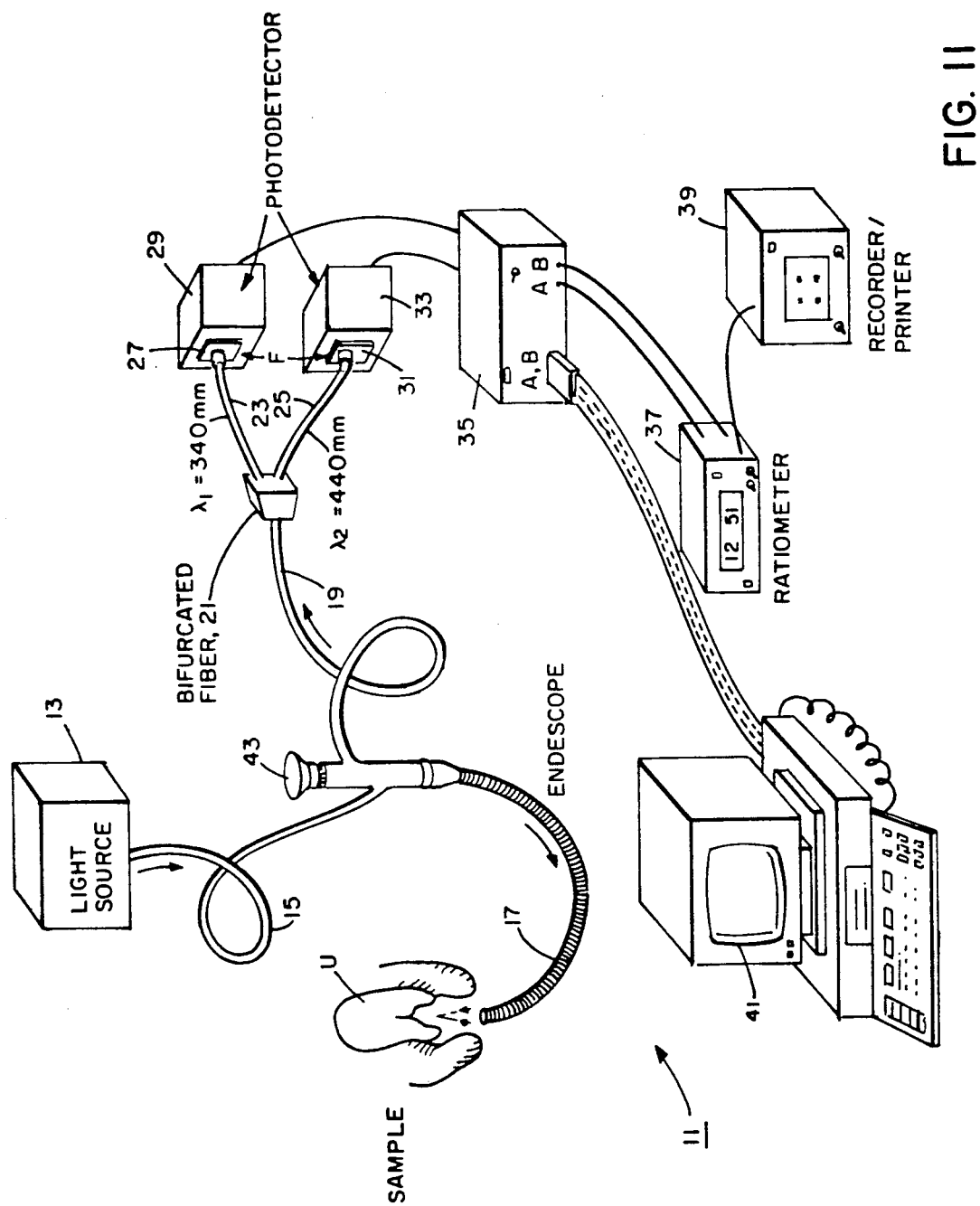
FIG. 11 is a simplified diagram of an apparatus according to this invention for testing a sample of tissue.

Referring now to FIG. 11, there is shown an embodiment of an apparatus 11 constructed according to this invention for testing a region of tissue to determine if the tissue is cancerous as opposed to benign or normal. By way of example, the tissue under test is in the uterus.

Monochromatic light at about 300 nm from a source 13 is transmitted through an optical fiber bundle 15 and a probe, which is in the form of an endoscope 17, and strikes the region of the uterus U to be examined. Source 13 may be, for example, a lamp and a 300 nm filter or a laser and a filter, or a laser such as an excimer laser which emits monochromatic light at about 300 nm. Fluorescence emitted from the region excited by light from source 13 is transmitted back through endoscope 17 to another optical fiber bundle 19 which is split through a divider 21 into two optical fiber bundles 23 and 25.

Light transmitted along optical fiber bundle 23 and passing through a 340 nm narrow band filter 27 strikes a photodetector 29 and light transmitted along optical fiber bundle 25 and passing through a 440 nm narrow band filter 31 strikes a photodetector 33.

The output of photodetectors 29 and 33 are fed into an analog to digital converter 35 having two outputs. One output is fed into a ratiometer 37 where a ratio of the two photodetector signals is taken. The output signal from ratiometer 37 is connected to a recorder or printer 39 for display. The other output is fed into a computer 41.

An eyepiece 43 is included to observe the area being examined.

Instead of an endoscope 17, the probe may comprise an optical fiber bundle inside a needle for use in probing i.e. penetrating, directly inside a tissue such as the breast for direct optical biopsy. Also, instead of an analog to digital converter and a computer, the outputs from the two photodetectors could be fed either to a difference circuit or a divider circuit and the output from those circuits diplayed by a suitable display.

Figure 12:
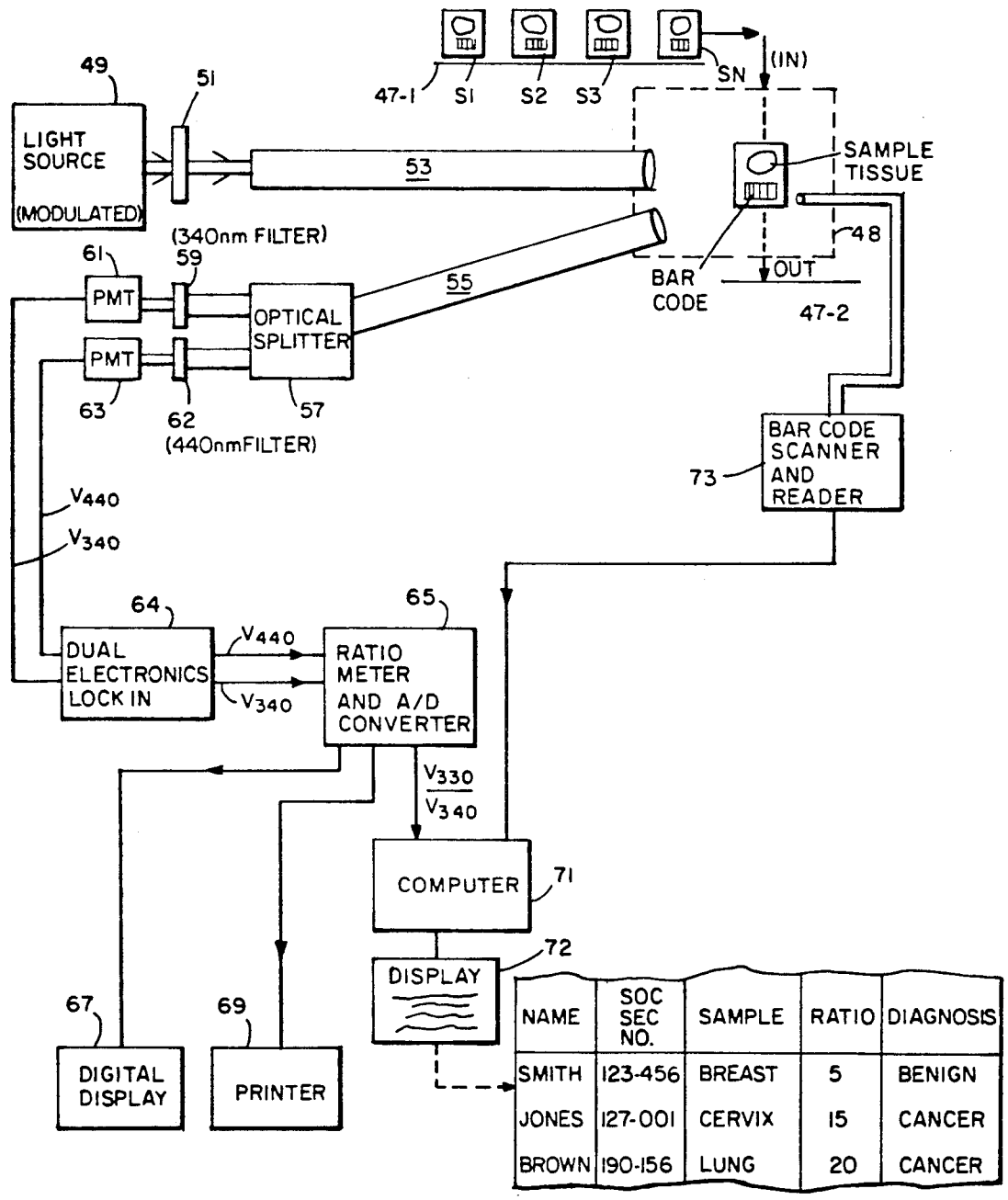
FIG. 12 is a simplified diagram of an optical biopsy system.

Referring now to FIG. 12 there is shown an optical biopsy system 45 according to this invention.

Samples S1, S2, S3 and Sn to be tested, identified by bar codes, are transported into an out of a sample chamber 47 by a conveyor system 47-1, 47-2.

A modulated beam of light from a source 49 is filtered by a 300 nm filter 51 and then transmitted by transmission optics 53 to sample chamber 48 where it strikes the sample under test. The beam is a modulated beam so as to reduce noise. Source 49 may be a lamp and a chopper. Transmission optics 53 may be a lens system or an optical fiber bundle. Light emitted from the sample is transmitted by collection optics 55, which may also be a lens system or an optical fiber bundle, to an optical beam splitter 57 where it is split into two beams. One beam is filtered by a 340 nm filter 59 and strikes a first photodetector 61. The other beam is filtered by a 440 nm filter 62 and strikes a second photodetector 63. The outputs of the two photodetectors 61 and 63 are fed into dual lock in amplifier electronics 64 which locks in on the frequency of modulation of source 49. The two outputs from electronics 64 are fed into a ratio meter and digitizer unit 65 which takes the ratio of the two signals and digitizes it. The output of ratio meter and digitizer unit 65 is fed into a digital display 67, into a printer 69 and into a computer 71. Computer 71 is connected to a display 72. Computer 71 also receives sample identification details from a bar code scanner and reader 73.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. Apparatus for determining if tissue is cancerous as opposed to benign or normal comprising:
    a. a source of monochromatic light for illuminating a tissue at a wavelength which will fluoresce at wavelengths where the intensity for cancerous tissue and that of benign or normal tissue are different;
    b. a pair of photodetector assemblies for measuring the intensity of light emitted from said tissue at two different wavelengths, each photodetector assembly including a photodetector and a filter, one filter being constructed to pass light at about 340 nm and the other at about 440 nm, each filter having a bandwidth of about 30 nm.;
    c. a length of optical fiber bundle for transmitting said fluorescent light from said tissue to said pair of photodetector assemblies;
    d. means coupled to said pair of photodetector assemblies for producing a processed signal corresponding to the signals from the pair of photodetector assemblies, and
    e. means for displaying said processed signal.

2. A method for determining if tissue is cancerous as opposed to benign or normal comprising:
    a. exciting a tissue to be examined with a beam of light that is at least substantially monochromatic, and at a wavelength between about 260 and 315 nm, whereby native fluorescence is emitted from the tissue,
    b. measuring the intensity of the native flurorescence at two wavelengths, one wavelength being about 340 nm and the other wavelength being about 440 nm, and
    c. determining if the tissue is cancerous as opposed to benign or normal in accordance with said measurements at said two wavelengths.

* * * * *